United States Statutory Invention Registration [19]

[11] Reg. Number: H676

Sheridan [43] Published: Sep. 5, 1989

[54] PRODUCTION OF UREA FLUOROSILICATE

[75] Inventor: Richard C. Sheridan, Sheffield, Ala.

[73] Assignee: Tennessee Valley Authority, Muscle Shoals, Ala.

[21] Appl. No.: 112,784

[22] Filed: Oct. 26, 1987

[51] Int. Cl.[4] ..... C07C 127/01
[52] U.S. Cl. ..... 564/63
[58] Field of Search ..... 564/63, 383

[56] References Cited

U.S. PATENT DOCUMENTS 4,461,913 7/1984 Lewis et al. ..... 564/63

*Primary Examiner*—John F. Terapane
*Assistant Examiner*—Valerie Fee
*Attorney, Agent, or Firm*—Robert A. Petrusek

[57] ABSTRACT

A process for producing urea fluorosilicate, $[(NH_2)_2CO]_4 \cdot H_2SiF_6$, a composition eminently suitable for use as a fungicide in the prevention and control of wheat stem rust. The method involves mixing urea and fluorosilicic acid derived from by-product fluorine in a mole ratio of urea:fluorosilicate acid in the range from about 3.5:1 to about 4.5:1 and thereafter dewatering the resulting solution to produce a concentrated solution of urea fluorosilicate. Solid urea fluorosilicate is subsequently obtained by evaporation of the remaining water which is conveniently effected by introducing the resulting solution or melt to concentrator means, or alternatively into a heated, moving bed of preformed granular urea fluorosilicate.

15 Claims, 1 Drawing Sheet

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

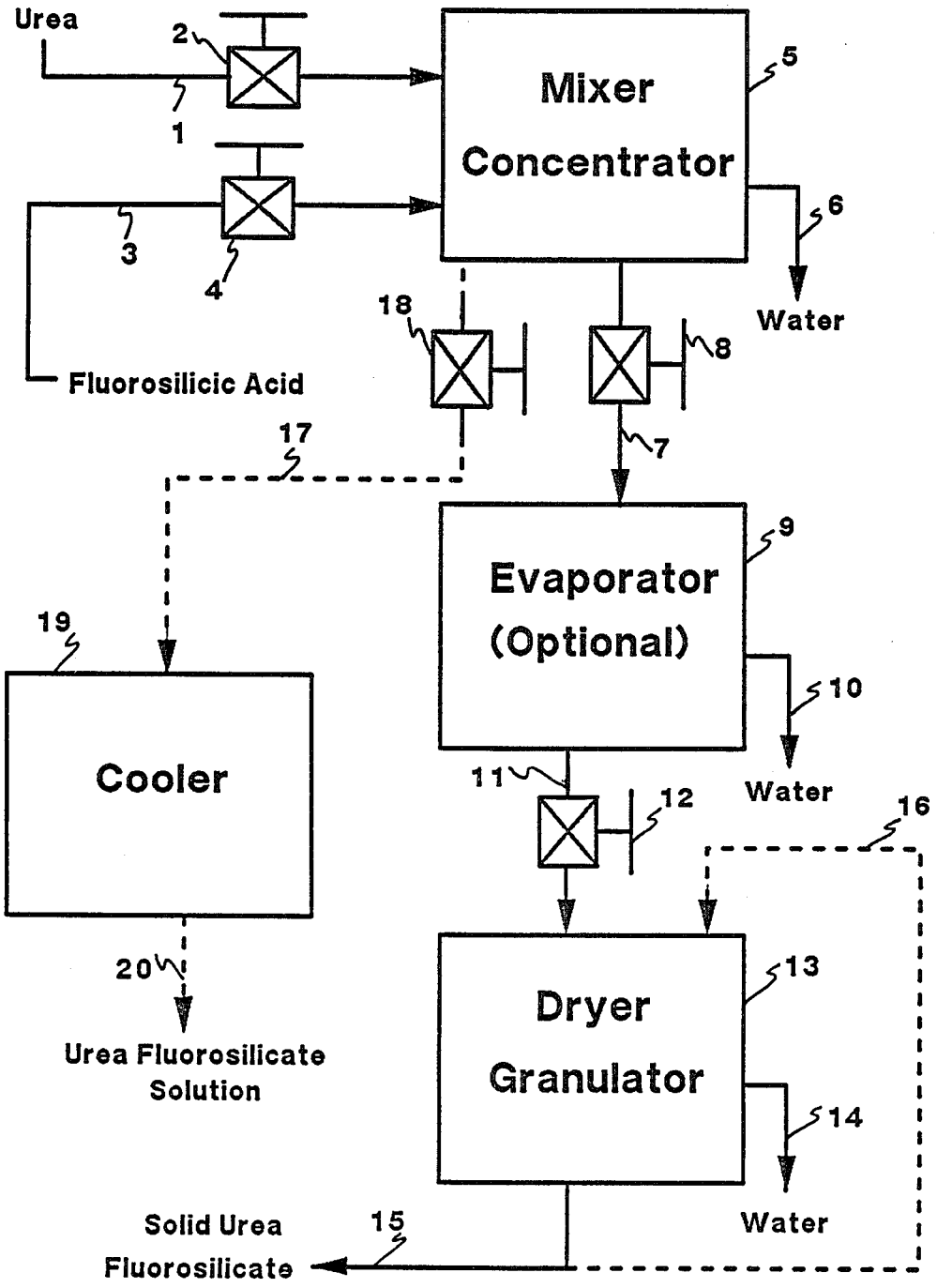
Urea
2
1
Mixer
Concentrator
5
6
Water
3
4
18
8
Fluorosilicic Acid
17
7
9
Evaporator
(Optional)
19
10
Cooler
11
12
Water
16
20
13
Dryer
Granulator
Urea Fluorosilicate
Solution
14
Solid Urea
Fluorosilicate
15
Water

PRODUCTION OF UREA FLUOROSILICATE

INTRODUCTION

The present invention relates to a new novel, and improved process for the production of urea fluorosilicate, a chemical compound which is eminently suitable for use as a fungicide in the prevention and treatment of wheat seem rust, a disease which occurs in most of the wheat-producing areas of the world. While such rust is a major disease of wheat in many countries, and only a minor disease in others, on a world basis it has probably been the most destructive of all wheat diseases for many centuries. Stem rust can, in less than a month, totally destroy millions of hectares of a seemingly healthy crop of wheat with an anticipated high-yield potential. Epidemics of these types have occurred in nearly every country wherein wheat is grown. Although numerous methods have been tried to control the disease, but none have proved to be completely satisfactory. After the organism is established in the host tissue, it is generally recognized by those skilled in this art that the only practical method for eradication of such stem rust is the application of fungicidal chemical compounds, including (he compound which is the subject and product of the instant invention.

BACKGROUND OF THE INVENTION

1. Field of the Invention

This invention pertains to methods and means for the production of urea fluorosiiicate, a chemical compound having the formula $[(NH_2)_2CO]_4.H_2SiF_6$, by new and improved processes employing, for the feedstock thereto, urea and fluorosilicic acid, said fluorosilicic acid being a by-product of the phosphate fertilizer industry. The mode of operation of the instant invention involves (1) reaction of urea and aqueous fluorosilicic acid; (2) concentration of the resulting aqueous solution of urea fluorosilicic acid; and, if desired, (3) crystallization of the product urea fluorosilicate as a solid.

2. Description of the Prior Art

Numerous prior art investigators have discovered, taught, and disclosed a number of me(hods for trying to overcome, or otherwise circumvent the problems associated with widespread occurrence of wheat stem rust, including improving upon the process for the production of urea fluorosilicate. For instance, according to the teachings of Zeying Zhang et al. [*Hua Hsueh Tung Pao.* 1981, (3) 142–143; *Kexue Tongbao* 1982, 27 (11, 658–62; *Kexue Tongbao,* 1983, 28 (7), 905–910 ] urea flourosilicate having the formula $[(NH_2)_2CO]_4.H_2SiF_6$ is a highly effective and practical agent for prevention and control of wheat stem rust. The compound is highly soluble and its concentrated solutions are relatively noncorrosive in comparison to those of concentrated fluorosilicic acid. The production and use of urea fluorosilicate has been extremely limited because heretofore no practical process was or has been available for its economical production. The only known method for its preparation, used by Zhang et al. supra, is based on the following equation $$4(NH_2)_2CO+2SiF_4+4CH_3OH=[(NH_2)_2CO]_4.H_2SiF_6+2HF+Si(OCH_3)_4$$

and requires the use of methyl alcohol and silicon tetrafluoride as raw materials. The yield of product is only 50 percent, based on silicon fluoride, even under the best of operating conditions. Furthermore, large amounts of by-products, namely hydrogen fluoride and methoxysilane, are produced which require additional processing, recovery, and disposal.

Other investigators have studied the solubility of urea in hexafluorosilicic acid [B. A. Beremzhanov. N. N. Nurakhmetov, A. Tashenov, and F. O. Suyundikova, *Russian Journal of Inorganic Chemistry.* 32 (1), 146, (1987)]. They reported the formation of diurea dihydrogen hexafluorosilicate and tetraurea dihydrogen hexafluorosilicate, but gave no conditions for isolation and purification of these compounds. They reported no chemical analyses, X-ray powder diffraction patterns, refractive indices, infrared absorption data, or other properties to characterize and identify their products. Consequently, their results add but little to the pool of information already existing on urea fluorosilicate, i.e., that shown by Zhang et al. supra.

It is obvious, therefore, that a need exists for the development of an improved process for the practical and economical production of urea fluorosilicate, particularly a process that utilizes low-cost, readily available fluorosilicic acid produced as a by-product in the acidulation of phosphate rock.

Phosphate rock, also known as fluoroapatite, is mined in huge quantities in several countries throughout the world and used in the production of fertilizers, phosphoric acid, and other phosphate compounds. Fluoroapatite usually contains 3 to 4 percent fluorine and a very significant amount of this fluorine is evolved as gaseous effluent in the production of fertilizers. The exhaust gases are ordinarily scrubbed in water so as to obtain a solution of fluorosilicic acid. The resulting scrubber solution usually contains 20 to 28 percent $H_2SiF_6$ . Many producers dispose of this potentially valuable fluorosilicate as waste material because of quite limited uses for it. Thus, it is highly desirable, from both an economical and environmental viewpoint, to find new uses for such by-product fluorine resulting from the various process operations practiced in the fertilizer industry.

SUMMARY OF THE INVENTION

According to the teachings of the present invention, such urea fluorosilicate is produced by a process which comprises reacting fluorosilicic acid prepared from by-product fluorine with urea to thereby yield an aqueous solution of urea fluorosilicate which is subsequently dewatered to ultimately produce either a concentrated product solution or a crystalline product. As noted supra, the only starting materials required as feedstock to the instant, unique, and novel process are urea, which is a commercial fertilizer produced in massive quantities, and fluorosilicic acid, large quantities of which are readily available as a cheap and economical by-product derived from the phosphate fertilizer industry.

OBJECTS OF THE INVENTION

Accordingly, it is therefore a principal object of the present invention to develop new and/or improve on existing methods for the production of urea fluorosilicate, a valuable fungicide, from inexpensive raw materials such as urea and by-product fluorosilicic acid.

Another object of the present invention is to develop new and/or improve on existing methods for the production of urea fluorosilicate, a valuable fungicide, from inexpensive raw materials such as urea and by-product fluorosilicic acid and to provide from such improved method for producing such urea fluorosilicate yields upwards of nearly 100 percent.

Still another object of the present invention is to develop new and/or improve on existing methods for the production of urea fluorosilicate, a valuable fungicide, from inexpensive raw materials such as urea and by-product fluorosilicic acid and to provide from such improved method for producing such urea fluorosilicate yields upwards of about 100 percent and to recover said urea fluorosilicate as a noncorrosive highly-concentrated liquid solution which can be conveniently pumped, transported, and stored.

A still further object of the present invention is to develop new and/or improve on existing methods for the production of urea fluorosilicate, a valuable fungicide, from inexpensive raw materials such as urea and by-product fluorosilicic acid and to provide in such improved method for producing such urea fluorosilicate yields upwards of about 100 percent and to recover as a crystalline solid product said urea fluorosilicate from aqueous solutions by employing the use of rather simple dewatering and solidification techniques.

Still further and more general objects and advantages of the present invention will appear from the more detailed description set forth below, it being understood, however, that this more detailed description is given by way of illustration and explanation only, and not necessarily by way of limitation since various changes therein may be made by those skilled in the art without departing from the true spirit and scope of the present invention.

DESCRIPTION OF THE DRAWING

My invention, together with further objects and advantages thereof, will be better understood from a consideration of the following description taken in connection with the accompanying drawing in which:

The FIGURE is a flowsheet in box form generally illustrating the principles of my novel process which results in a urea fluorosilicate product or products having the desirable properties mentioned above.

Referring now more specifically to the FIGURE, vessel 5 represents any means suitable for containing. mixing. and heating the charge to be introduced thereinto. A stream of fluorosilicic acid (25–30% preferred) from a source not shown (such as by-product fluorine from a phosphate plan) is introduced via line 3 and means for control of flow 4 into vessel 5. Simultaneously a stream of solid urea or concentrated urea solution (75–99% preferred) from a source not shown (such as a urea synthesis plant) is introduced via line 1 and means for control of flow 2 into vessel 5 to form therein, after dissolution of the solid urea (if used) and commingling of the charge, an aqueous solution of urea fluorosilicate. Water vapor is expelled from vessel 5 via line 6 as heat is applied thereto. The resulting solution of urea fluorosilicate is thereby concentrated in vessel 5 to an intermediate level such as in the range from about 65 to about 75 percent and then discharged via line 7 and means for control of flow 8 or alternatively via line 17, and means for control of flow 18 for further processing into the desired products, either solid urea fluorosilicate and/or fluid urea fluorosilicate solution. According to the practice of one embodiment of the present invention, the intermediate urea fluorosilicate solution is fed via line 7 and means of control 8 into evaporation vessel 9 wherein additional water is driven off and vented via line 10, by application of heat and/or vacuum, or by use of air sparging to increase the concentration of urea fluorosilicate up to the range from about 85 to about 95 percent. The resulting urea fluorosilicate solution in vessel 9 is then introduced via line 11 and means for control of flow 12 into dryer or granulator vessel 13 for purposes of removal therein of the remaining water via line 14 and the production of solid urea fluorosilicate which is removed as product via line 15. Vessel 13 may, for example, comprise a revolving drum-type dryer to which urea fluorosilicate solution is applied as a film for rapid evaporation of the remaining water and formation of a solid which is scraped off by a stationary knife. Alternately, vessel 13 may comprise a granulator containing a moving bed of hot, granular, preformed urea fluorosilicate onto which the incoming fluid, i.e., urea fluorosilicate solution, is introduced as a spray to promote rapid drying and crystallization. Optional operation of dryer-granulator 13 may involve the use of recycle urea fluorosilicate which is withdrawn via line 16 as a portion of the product, such as the oversize and undersize fractions, and reintroduced into vessel 13 after crushing or grinding not shown, of the oversize fraction. At least a portion of the solid urea fluorosilicate produced in vessel 13 is withdrawn via line 15 and collected as a dry. free-flowing product.

Referring now to another embodiment of my invention, a concentrated solution of urea fluorosilicate containing in the range from about 60 to about 75 percent urea fluorosilicate is withdrawn from vessel 5 via line 17 and means for control of flow 18 and introduced into cooling means 19. The resulting cooled urea fluorosilicate solution is collected from cooling means 19 via line 20 as a fluid, highly concentrated, stable solution suitable for shipment, storage, or immediate use.

DESCRIPTION OF THE PREFERRED EMBODIMENTS

In practicing the various embodiments and/or options available in the pursuit of my invention, as described in detail and in conjunction with the FIGURE supra, a reaction temperature in the range from about 25° C. to about 135° C. and preferably in the range from about 50° C. to about 90° C., is utilized in the reactor to expel excess water originally supplied by and derived from the feed aqueous fluorosilicic acid. The length of time required to accomplish this will vary, depending on the initial concentration of fluorosilicic acid charged thereto and the reaction conditions used therein, but the time and temperature conditions should be adjusted to reduce the water content of the urea fluorosilicate solution down to the range from about 15 to about 30 percent. The remainder of the free water is driven off during the subsequent crystallization and drying process. Concentrated urea solution containing in the range from about 75 to about 99 weight percent urea, by weight, such as that produced as an intermediate in the manufacture of dry, solid urea is a suitable source of the urea fed to my process; however, concentrations in the range from about 90 to about 100 percent urea, by weight are preferred. The concentration of fluorosilicic acid utilized as feedstock to my process may range from about 15 percent to about 35 percent by weight; however, at concentrations below about 15 percent, I have found that too much water will be present for effecting an economical and convenient evaporation step, while at concentrations above about 35 percent by weight, the fluorosilicic acid feed develops an undesirable relatively high vapor pressure of silicon fluoride. Consequently, a concentration in the range from about 25 to about 32 percent is preferred. The temperature of the crystallizer may range from about 25° C. to about 95° C., preferably from about 45° C. to about 75° C. At temperatures below about 25° C., the reaction mixture will not dry at a rate practical for the economical operation of my process, while at temperatures in excess of about 95° C. the urea fluorosilicate is above its freezing or solidification temperature. The crystallization and drying process steps of the instant invention may be conveniently expedited by recycling some product urea fluorosilicate to provide a preformed, rolling or cascading bed into which the concentrated molten urea fluorosilicate intermediate is introduced and from which crystalline urea fluorosilicate is withdrawn, dried further if needed, and collected as product. The recycle ratio of urea fluorosilicate will vary, depending on the temperature of the crystallizer and the water content of the feed material; however in general, the preferred range of recycle to feed material ranges from about 1:1 to about 2:1.

The concentrated solutions of urea fluorosilicate prepared by the practice of the present invention may contain up to about 75 percent $[(NH_2)_2CO]_4 \cdot H_2SiF_6$ and stable at 0° C. for extended periods of time i.e., for at least several months without the formation of solids or crystals which tend to clog pumps and spray nozzles of application equipment. The mole ratio of urea to fluorosilicic acid in the charge may range from about 3.5:1 to about 4.5:1, but the preferred mole ratio is in the range from about 3.9:1 to about 4.1:1. A mole ratio of about 4:1 will best permit the attainment of pure urea fluorosilicate having the chemical formula $[(NH_2)_2CO].H_2SiF_6$.

EXAMPLES

In order that those skilled in the art may better understand how the present invention may be practiced and more fully and definitely understood, the following examples are given by way of illustration only and not necessarily by way of limitation.

EXAMPLE I

Urea (24.0 grams) and 30 percent fluorosilicic acid (48.0 grams) were mixed in a crystallizing dish at room temperature and allowed to stand overnight. No crystals or precipitates formed, and no heat or gaseous products were evolved. No solids formed when the solution was chilled to 0° C. It was then allowed to evaporate at room temperature in a watch glass. After a period of one week a crystalline mass had formed in the container. The product was collected, washed with alcohol, and dried. The yield was 38.23 grams or 99.5 percent recover for $[(NH_2)_2CO]_4.H_2SiF_6$. Polarized light microscopy showed that the product was a homogeneous crystalline substance with unique optical properties. The composition of the product was proven by mass spectrometry and chemical analysis and is compared below in Table I with the theoretically predicted composition.

TABLE I

| Composition, Weight Percent | | |
|---|---|---|
| Element | Found in Product | Theoretical for $[(NH_2)_2CO]_4.H_2SiF_6$ |
| N | 28.9 | 29.15 |
| F | 28.8 | 29.65 |
| Si | 7.34 | 7.31 |

TABLE I-continued

| Composition, Weight Percent | | |
|---|---|---|
| Mole ratio | Found in Product | Theoretical for $[(NH_2)_2CO]_4.H_2SiF_6$ |
| N:F | 1.35 | 1.33 |
| N:Si | 7.89 | 8.00 |
| F:Si | 5.80 | 6.00 |
| Optical Properties | | |
| Crystal | Biaxial negative, orthorhombic | |
| Refractive indices | $\alpha$ = 1.380 | |
| | $\beta$ = 1.480 | |
| | Y = 1.520 | |

The optical properties of my new and unique urea fluorosilicate are distinctly different from those corresponding to tetragonal, uniaxial crystals as disclosed by Zhang et al. supra. Furthermore, the X-ray diffraction line of my product do not match those predicted by Zhang et al.'s unit cell values.

For support of this contention, listed below in Tables II and III are the X-ray powder diffraction patterns obtained on samples of materials produced according to the teachings of the instant invention and a listing of all possible lines which are possible from computer predictions determined by input thereto of the unit cell parameters and other characteristics taught by Zhang et al., respectively.

TABLE II

X-RAY POWDER DIFFRACTION DATA FOR $[(NH_2)_2CO]_4.H_2SiF_6$ USING CuK$\alpha$ RADIATION WITH WAVE LENGTH EQUAL TO 1.54059 Å (Complete Pattern)

| d | I/Io | d | I/Io |
|---|---|---|---|
| 8.883 | 8 | 2.2716 | 1 |
| 8.321 | 51 | 2.2491 | 1 |
| 8.128 | 5 | 2.2140 | 1 |
| 6.726 | 18 | 2.2006 | 1 |
| 5.557 | 12 | 2.1663 | 1 |
| 5.004 | 4 | 2.1305 | 4 |
| 4.815 | 38 | 2.1160 | 1 |
| 4.4316 | 9 | 2.1049 | 2 |
| 4.2900 | 60 | 2.0737 | 1 |
| 4.1500 | 3 | 2.0583 | 1 |
| 4.0774 | 6 | 2.0426 | 11 |
| 3.8288 | 11 | 2.0159 | 1 |
| 3.5773 | 4 | 1.9906 | 1 |
| 3.5412 | 100 | 1.9388 | 1 |
| 3.4389 | 2 | 1.9107 | 1 |
| 3.3575 | 19 | 1.8760 | 2 |
| 3.3156 | 10 | 1.8600 | 1 |
| 3.2183 | 4 | 1.8290 | 1 |
| 3.0767 | 9 | 1.8052 | 1 |
| 3.0328 | 1 | 1.7926 | 1 |
| 2.9707 | 5 | 1.7691 | 5 |
| 2.9411 | 6 | 1.7601 | 1 |
| 2.8639 | 3 | 1.7429 | 1 |
| 2.8460 | 4 | 1.7300 | 1 |
| 2.7880 | 7 | 1.7210 | 1 |
| 2.7617 | 1 | 1.6705 | 2 |
| 2.6993 | 2 | 1.6561 | 1 |
| 2.6656 | 1 | 1.6263 | 1 |
| 2.6300 | 2 | 1.6193 | 1 |
| 2.6107 | 5 | 1.6000 | 1 |
| 2.5106 | 1 | 1.5850 | 2 |
| 2.4962 | 1 | 1.5762 | 2 |
| 2.4468 | 1 | 1.5433 | 1 |
| 2.4282 | 1 | 1.5151 | 1 |
| 2.4034 | 2 | 1.5000 | 1 |
| 2.3843 | 3 | 1.4710 | 1 |
| 2.3423 | 6 | 1.4110 | 1 |
| | | 1.4062 | 1 |
| | | 1.1560 | 1 |

The unit cell parameters for tetragonal urea fluorosilicate (a=b=9.263Å and C=17.898Å) reported by Zhang et al. [*Kexue Tongbao* 28 (No. 7), 905–190 (July 1983)] were used to generate d-spacings for their compound by utilization of a computer software routine known as IDEX, available on the Scintag PAD automated X-ray diffraction system. NOTE: Any references made herein to materials and/or apparatus which are identified by means of trademarks, tradenames, etc., are included solely for the convenience of the reader and are not intended as or to be construed an endorsement of said materials and/or apparatus. The routine uses a standard crystallographic formula $$d = \frac{1}{\sqrt{\frac{h^2}{a^2} + \frac{k^2}{b^2} + \frac{l^2}{c^2}}}$$

to calculate all possible d-spacings for Zhang et al.'s product, where, as noted above a=b=9.263Å, c=17.898Åand h, k, and l are symbolic representations for the Miller indices as noted below.

A set of three or four symbols (letters or integers) used to define the position and orientation of a crystal face or internal crystal plane. The indices are determined by expressing, in terms of lattice constants, the reciprocals of the intercepts of the face or plane on the three crystallographic axes, and reducing (clearing fractions) if necessary to the lowest integers retaining the same ratio. When the exact intercepts are unknown, the general symbol (hkl) is used for the indices, where h, k, and l are respectively the reciprocals of rational but undefined intercepts along the a, b, and c crystallographic axes. In the hexagonal system, the Miller indices are (hkil); these are known as the Miller-Bravais indices. Conventionally, indices designating individual crystal faces are enclosed in parentheses; complete crystal forms, in braces; crystal zones, in square brackets; and crystallographic lines, in greater than/less than symbols. To denote the interception at the negative end of an axis, a line is placed over the appropriate index, as $(1\bar{1}1)$. The indices were proposed by William H. Miller (1801–1880), English mineralogist.

TABLE III

All Possible d-spacings Generated from the Unit Cell Data for Urea Fluorosilicate reported by Zhang et al.

| d | h | k | l |
|---|---|---|---|
| 8.2461 | 1 | 0 | 1 |
| 6.5281 | 1 | 1 | 0 |
| 6.4199 | 1 | 0 | 2 |
| 6.1631 | 1 | 1 | 1 |
| 5.2983 | 1 | 1 | 2 |
| 5.0103 | 1 | 0 | 3 |
| 4.6210 | 2 | 0 | 0 |
| 4.4926 | 2 | 0 | 1 |
| 4.4692 | 0 | 0 | 4 |
| 4.4106 | 1 | 1 | 3 |
| 4.1495 | 2 | 1 | 0 |
| 4.1061 | 2 | 0 | 2 |
| 4.0395 | 2 | 1 | 1 |
| 3.7521 | 2 | 1 | 2 |
| 3.6996 | 1 | 1 | 4 |
| 3.6551 | 2 | 0 | 3 |
| 3.4027 | 2 | 1 | 3 |
| 3.3376 | 1 | 0 | 5 |
| 3.2733 | 2 | 2 | 0 |
| 3.2236 | 2 | 2 | 1 |
| 3.1420 | 1 | 1 | 5 |
| 3.0772 | 2 | 2 | 2 |
| 3.0452 | 3 | 0 | 1 |
| 2.9251 | 3 | 1 | 0 |
| 2.9154 | 3 | 0 | 2 |

TABLE III-continued

All Possible d-spacings Generated from the Unit Cell Data for Urea Fluorosilicate reported by Zhang et al.

| d | h | k | l |
|---|---|---|---|
| 2.8887 | 3 | 1 | 1 |
| 2.8739 | 2 | 2 | 3 |
| 2.8382 | 1 | 0 | 6 |
| 2.7868 | 3 | 1 | 2 |
| 2.7428 | 3 | 0 | 3 |
| 2.7119 | 1 | 1 | 6 |
| 2.6393 | 2 | 2 | 4 |
| 2.6292 | 3 | 1 | 3 |
| 2.5694 | 3 | 2 | 0 |
| 2.5410 | 3 | 0 | 4 |
| 2.5075 | 2 | 0 | 6 |
| 2.4671 | 3 | 2 | 2 |
| 2.4510 | 3 | 1 | 4 |
| 2.4227 | 2 | 1 | 6 |
| 2.4147 | 2 | 2 | 5 |
| 2.3843 | 1 | 1 | 7 |
| 2.3603 | 3 | 2 | 3 |
| 2.3359 | 3 | 0 | 5 |
| 2.3158 | 4 | 0 | 0 |
| 2.2989 | 4 | 0 | 1 |
| 2.2667 | 3 | 1 | 5 |
| 2.2480 | 4 | 1 | 0 |
| 2.2406 | 2 | 0 | 7 |
| 2.2317 | 4 | 1 | 1 |
| 2.2033 | 2 | 2 | 6 |
| 2.1827 | 3 | 3 | 0 |
| 2.1772 | 1 | 0 | 8 |
| 2.1667 | 3 | 3 | 1 |
| 2.1596 | 4 | 0 | 3 |
| 2.1433 | 3 | 0 | 6 |
| 2.1198 | 3 | 3 | 2 |
| 2.1028 | 4 | 1 | 3 |
| 2.0897 | 3 | 1 | 6 |
| 2.0733 | 4 | 2 | 0 |
| 2.0581 | 4 | 0 | 4 |
| 2.0490 | 3 | 3 | 3 |
| 2.0174 | 4 | 2 | 2 |
| 2.0071 | 4 | 1 | 4 |
| 1.9705 | 2 | 1 | 8 |
| 1.9637 | 3 | 3 | 4 |
| 1.9549 | 4 | 2 | 3 |
| 1.9453 | 3 | 2 | 6 |
| 1.9258 | 3 | 1 | 7 |
| 1.9043 | 4 | 1 | 5 |
| 1.8792 | 4 | 2 | 4 |
| 1.8622 | 3 | 3 | 5 |
| 1.8518 | 4 | 3 | 0 |
| 1.8468 | 2 | 2 | 8 |
| 1.8426 | 5 | 0 | 1 |
| 1.8285 | 4 | 0 | 6 |
| 1.8162 | 5 | 1 | 0 |
| 1.8110 | 3 | 0 | 8 |
| 1.8068 | 5 | 1 | 1 |
| 1.7953 | 4 | 1 | 6 |
| 1.7806 | 5 | 1 | 2 |
| 1.7690 | 4 | 3 | 3 |
| 1.7633 | 3 | 3 | 6 |
| 1.7565 | 1 | 0 | 10 |
| 1.7378 | 5 | 1 | 3 |
| 1.7279 | 1 | 1 | 10 |
| 1.7190 | 5 | 2 | 0 |
| 1.7150 | 4 | 0 | 7 |
| 1.7119 | 5 | 0 | 4 |
| 1.7015 | 4 | 2 | 6 |
| 1.6891 | 5 | 2 | 2 |
| 1.6858 | 3 | 2 | 8 |
| 1.6712 | 3 | 0 | 9 |
| 1.6592 | 3 | 3 | 7 |
| 1.6515 | 5 | 2 | 3 |
| 1.6459 | 3 | 1 | 9 |
| 1.6371 | 4 | 4 | 0 |
| 1.6317 | 4 | 4 | 1 |
| 1.6203 | 5 | 1 | 5 |
| 1.6108 | 4 | 4 | 2 |
| 1.6059 | 5 | 2 | 4 |
| 1.6021 | 1 | 0 | 11 |
| 1.5878 | 5 | 3 | 0 |
| 1.5824 | 5 | 3 | 1 |

TABLE III-continued

All Possible d-spacings Generated from the Unit Cell Data for Urea Fluorosilicate reported by Zhang et al.

| d | h | k | l |
|---|---|---|---|
| 1.5793 | 1 | 1 | 11 |
| 1.5738 | 3 | 2 | 9 |
| 1.5698 | 2 | 2 | 10 |
| 1.5637 | 5 | 3 | 2 |
| 1.5512 | 5 | 1 | 6 |
| 1.5447 | 6 | 0 | 0 |

Example II

Urea (60.0 grams) and fluorosilicic acid (120.0 grams) were mixed in a crystallizing dish and heated in a forced draft oven maintained at 50° C. for 24 hours. The resulting product was observed to be a clear, transparent melt which crystallized rapidly upon removal from the oven and treatment with a seed crystal of urea fluorosilicate. The product was crushed and dried in a vacuum desiccator. The yield was 97.2 grams which corresponds to a predicted recovery of 96.0 grams, the additional weight being due to the seed crystal and traces of water left on the product. The product was identical to that produced in Example I supra when examined under the microscope and by X-ray diffraction.

EXAMPLE III

In a crystallizing dish, a mixture of urea (24.0 grams) and fluorosilicic acid (48.0 grams) was concentrated for 18 hours in a forced draft oven maintained at 50° C. to thereby yield a clear, transparent melt (43.56 grams).

The bulk of the melt (41.64 grams) was added in small portions to a preformed, rolling bed of granular urea fluorosilicate (80.2 grams) during a 35-minute period. Said rolling bed was effected in the laboratory by attaching a 600 ml stainless steel beaker by means of a flange and set screw to a shaft inclined about 45 degrees from the horizontal and rotated at about 48 rpm. The temperature of the bed was maintained at 65 to 70° C. by use of an electric heating jacket on the outside of said beaker during the addition of materials to the inclined and rotating beaker and for an additional period of about 15 minutes to complete the drying process. The product (121.8 grams) was a dry, granular, free-flowing material identical to that produced in Example I supra when examined under the microscope and by X-ray diffraction. The increase in weight (36.35 grams) corresponded to a yield of 98.9 percent based on the molten charge. Small portions (about 0.4 gram) of the product were lost by spillage and adherence to the reactor walls, thermometer, and so forth.

EXAMPLE IV

Solubility tests showed that solutions of urea fluorosilicate containing up to 76 percent urea fluorosilicate were stable, fluid, and free of crystals or other solids after storage at 0° C. for at least one week. The tests were carried out by dissolving different amounts of urea fluorosilicate in known amounts of water at 50° C. followed by cooling and subsequent storage in a cold room maintained at 0° C. The solutions were examined daily and shaken to encourage crystallization. No crystallization occurred in any of the solutions containing about 76 percent or lesser amounts of urea fluorosilicate. On the other hand, crystals of urea fluorosilicate formed in the more highly concentrated solutions. The liquid phases from these saturated solutions contained approximately 76 percent urea fluorosilicate. The crystals were identified by polarized light microscopy and X-ray powder diffraction methods.

INVENTION PARAMETERS

After sifting and winnowing through the data supra, as well as other results of tests and operation of my new, novel, process for producing urea fluorosilicate, I now present the acceptable and preferred parameters and variables as shown below.

| Variables | Operating Limits | Preferred Limits | Most Preferred Limits |
|---|---|---|---|
| Mole ratio $(NH_2)_2CO:H_2SiF_6$ | 3.5–4.5 | 3.9–4.1 | 4.00 |
| Concentration of feed $H_2SiF_6$ | 15–35 | 25–32 | 28–30 |
| Concentration of feed urea | 75–100 | 90–100 | 98–100 |
| Temperature, °C. in Mixer | 25–135 | 50–90 | 65–75 |
| Temperature, °C. in Evaporator | 35–125 | 65–110 | 85–95 |
| Temperature, °C. in Dryer | 25–95 | 45–85 | 60–70 |
| Recycle ratio | 0–5 | 0.5–3 | 1–2 |
| Concentration of liquid product, % | 50–90 | 65–85 | 70–80 |
| Time at temperature (Mixer), min.* | 3–5000 | 15–300 | 30–150 |
| Time at temperature (Evaporator), min.* | 3–600 | 6–300 | 15–150 |
| Time at temperature (Dryer), min.* | 5–300 | 10–150 | 20–100 |

*Temperature is the controlling factor with time thereat being in a dependent and inversely proportional relationship thereto.

While I have shown and described particular embodiments of my invention, modifications and variations thereof will occur to those skilled in the art. I wish it to be understood therefore that the appended claims are intended to cover such modifications and variations which are within the true scope and spirit of my invention.

What I claim as new and desire to secure by Letters Patent of the United States is:

1. An improved process for producing solid urea fluorosilicate in a form eminently suitable for use as a fungicide effective for the prevention and control of wheat stem rust which improved process comprises the steps of:

(a) introducing into mixing means predetermined quantities of urea and fluorosilicic acid, said urea ranging in concentration from about 75 to about 100 percent by weight, said fluorosicilic acid ranging in concentation from about 15 to about 35 percent by weight, and said predetermined quantities of said urea and said fluorosilicic acid proportionally selected so as to effect a mole ratio of $(NH_2)_2CO:H_2SiF_6$ ranging from about 3.5:1 to about 4.5:1 in the aqueous solution of urea fluorosilicate resulting in said mixing means;

(b) removing at least a portion of said resulting aqueous solution of urea fluorosilicate from said mixing means and introducing same into concentrating means;

(c) maintaining the temperature of the material in said concentrating means in the range from about 25° C. to about 135° C. and maintaining said concentrating means operatively connected to ambient atmospheric pressure for a period of time sufficient to thereby effect the removal of quantities of free water associated with said aqueous solution of urea fluorosilicate to thereby increase said solution's concentration up to a range from about 50 percent to about 90 percent by weight;

(d) removing at least a portion of the resulting concentrated aqueous urea fluorosilicate solution from said concentrating means and introducing same into crystallizing means;

(e) cooling said concentrated aqueous urea fluorosilicate solution introduced into said crystallizing means and forming crystals from said solution;

(f) removing at least a portion of the crystals formed in said crystallizing means to drying means wherein said introduced crystals are subjected to elevated temperatures ranging from about 25° C. to about 95° C.; and (g) removing from said drying means, as product, a virtually pure fluorosilicate having the formula $[(NH_2)_2CO{:}H_2SiF_6]\ [(NH_2)_2CO]_4.H_2SiF_6$.

2. The process of claim 1 wherein said mole ratio of urea to fluorosilicic acid ranges from about 3.9:1 to about 4.1:1, wherein the concentration of said urea introduced into said mixing means ranges from about 90 percent to about 100 percent by weight, and wherein the concentration of fluorosilicic acid introduced into said mixing means ranges from about 25 percent to about 32 percent by weight.

3. The process of claim 2 wherein the mole ratio of urea to fluorosilicic acid is maintained at about 4:1, wherein said concentration of urea fed to said mixing means ranges from about 98 to about 100 percent by weight, and wherein the concentration of said fluorosilicic acid introduced into said mixing means ranges from about 28 to about 30 percent by weight.

4. The process of claim 1, 2, or 3 wherein the temperature of said mixing means is maintained in the range from about 50° C. to about 90° C. and wherein the temperature in said dryer means ranges from about 45° C. to about

5. The process of claim 1, 2, or 3 wherein the temperature of said means is maintained in the range from about 65° C. to about 75° C. and wherein the temperature in said dryer means ranges from about 60° C. to about 70° C.

6. An improved process for producing solid urea fluorosilicate in a form eminently suitable for use as a fungicide effective for the prevention and control of wheat stem rust which process comprises the steps of:

(a) introducing into mixing means predetermined quantities of urea and fluorosilicic acid, said urea ranging in concentration from about 75 to about 100 percent by weight, said fluorosilicic acid ranging in concentration from about 15 to about 35 percent by weight, and said predetermined quantities of said urea and said fluorosilicic acid proportionally selected so as to effect a mole ratio of $(NH_2)_2CO{:}H_2SiF_6$ ranging from about 3.5:1 to about 4.5:1 in the resulting aqueous solution of urea fluorosilicate resulting in said mixing means;

(b) removing at least a portion of said resulting aqueous solution of urea fluorosilicate from said mixing means and introducing same into concentrating means;

(c) maintaining the temperature of the material in said concentrating means in the range from about 25° C. to about 135° C. and maintaining said concentrating means operatively connected to ambient atmospheric pressure for a period of time sufficient to thereby effect the removal of quantities of free water associated with said aqueous solution of urea fluorosilicate to thereby increase said solution's concentration up to a range from about 50 percent to about 90 percent by weight;

(d) removing at least a portion of the resulting concentrated urea fluorosilicate solution from said concentrating means and introducing same into contact with a moving bed of particulate solid urea fluorosilicate, said contact with said moving bed of particulate solid urea fluorosilicate being at a temperature ranging from about 35° C. to about 95° C.; and (e) removing water from said moving bed of particulate solid urea fluorosilicate maintained in step (d) supra to effect the formation of additional quantities therein of solid urea fluorosilicate as product.

7. The process of claim 6 wherein the recycle ratio of particulate urea fluorosilicate, added to said moving bed, to the quantity of concentrated aqueous urea fluorosilicate introduce thereto ranges, on a weight basis, upwards to about 5:1.

8. The process of claim 7 wherein said recycle ratio ranges from about 0.5:1 to about 3:1.

9. The process of claim 8 wherein said recycle ratio ranges from about 1:1 to about 2:1.

10. An improved process for producing liquid urea fluorosilicate in a form eminently suitable for use as a fungicide effective for the prevention and control of wheat stem rust which process comprises the steps of:

(a) introducing into mixing means predetermined quantities of urea and fluorosilicic acid, said urea ranging in concentration from about 75 to about 100 percent by weight, said fluorosilicic acid ranging in concentration from about 15 to about 35 percent by weight, and said predetermined quantities of said urea and said fluorosilicic acid proportionally selected so as to effect a mole ratio of $(NH_2)_2CO{:}H_2SiF_6$ ranging from about 3.5:1 to about 4.5:1 in the resulting aqueous solution of urea fluorosilicate resulting in said mixing means;

(b) removing at least a portion of said resulting aqueous solution of urea fluorosilicate from said mixing means and introducing same into concentrating means;

(c) maintaining the temperature of the material in said concentrating means in the range from about 25° C. to about 135° C. and maintaining said concentrating means operatively connected to ambient atmospheric pressure for a period of time sufficient to thereby effect the removal of quantities of free water associated with said aqueous solution of urea fluorosilicate to thereby increase said solution's concentration up to a range from about 70 percent to about 80 percent by weight;

(d) removing at least a portion of the resulting concentrated aqueous urea fluorosilicate solution from said concentrating means and introducing same into cooling means wherein said material is cooled to about ambient temperature and thereafter removed as urea fluorosilicate product solution.

11. The process of claim 10 wherein said mole ratio of urea to fluorosilicic acid ranges from about 3.9:1 to about 4.1:1, wherein the concentration of said urea in(-roduced into said mixing means ranges from about 90 percent to about 100 percent by weight, and wherein the concentration of fluorosilicic acid introduced into said mixing means ranges from about 25 percent to about 32 percent by weight.

12. The process of claim 11 wherein the mole ratio of urea to fluorosilicic acid is maintained at about 4:1 wherein said concentration of urea fed to said mixing means ranges from about 98 to about 100 percent by weight, and wherein the concentration of said fluorosilicic acid introduced into said mixing means ranges from about 28 to about 30 percent by weight.

13. The process of claim 10, 11, or 12 wherein the temperature of said mixing means is maintained in the range from about 50° C. to about 90° C.

14. The process of claim 10, 11, or 12 wherein the temperature of said mixing means is maintained in the range from about 65° C. to about 75° C.

15. A new composition of matter comprising a urea fluorosilicate in a form inently suitable for use as fungicide effective for the prevention and control of wheat stem rust having an empirical formula $(NH_2)_2CO]_4.H_2SiF_6$, which composition has the following unique X-ray powder diffraction pattern obtained by using CuKα radiation with wave length equal to 1.54059 Å:

| d | I/Io | d | I/Io |
|---|---|---|---|
| 8.883 | 8 | 2.2716 | 1 |
| 8.321 | 51 | 2.2491 | 1 |
| 8.128 | 5 | 2.2140 | 1 |
| 6.726 | 18 | 2.2006 | 1 |
| 5.557 | 12 | 2.1663 | 1 |
| 5.004 | 4 | 2.1305 | 4 |

-continued

| d | I/Io | d | I/Io |
|---|---|---|---|
| 4.815 | 38 | 2.1160 | 1 |
| 4.4316 | 9 | 2.1049 | 2 |
| 4.2900 | 60 | 2.0737 | 1 |
| 4.1500 | 3 | 2.0583 | 1 |
| 4.0774 | 6 | 2.0426 | 1 |
| 3.8288 | 11 | 2.0159 | 1 |
| 3.5773 | 4 | 1.9906 | 1 |
| 3.5412 | 100 | 1.9388 | 1 |
| 3.4389 | 2 | 1.9107 | 1 |
| 3.3575 | 19 | 1.8760 | 2 |
| 3.3156 | 10 | 1.8600 | 1 |
| 3.2183 | 4 | 1.8290 | 1 |
| 3.0767 | 9 | 1.8052 | 1 |
| 3.0328 | 1 | 1.7926 | 1 |
| 2.9707 | 5 | 1.7691 | 5 |
| 2.9411 | 6 | 1.7601 | 1 |
| 2.8639 | 3 | 1.7429 | 1 |
| 2.8460 | 4 | 1.7300 | 1 |
| 2.7880 | 7 | 1.7210 | 1 |
| 2.7617 | 1 | 1.6705 | 2 |
| 2.6993 | 2 | 1.6561 | 1 |
| 2.6656 | 1 | 1.6263 | 1 |
| 2.6300 | 2 | 1.6193 | 1 |
| 2.6107 | 5 | 1.6000 | 1 |
| 2.5106 | 1 | 1.5850 | 2 |
| 2.4962 | 1 | 1.5762 | 2 |
| 2.4468 | 1 | 1.5433 | 1 |
| 2.4282 | 1 | 1.5151 | 1 |
| 2.4034 | 2 | 1.5000 | 1 |
| 2.3843 | 3 | 1.4710 | 1 |
| 2.3423 | 6 | 1.4110 | 1 |
| | | 1.4062 | 1 |
| | | 1.1560 | 1 |

* * * * *